US008779208B2

(12) United States Patent
Barnicki et al.

(10) Patent No.: US 8,779,208 B2
(45) Date of Patent: Jul. 15, 2014

(54) PROCESS FOR REDUCING EMISSIONS OF VOLATILE ORGANIC COMPOUNDS FROM THE KETONIZATION OF CARBOXYLIC ACIDS

(75) Inventors: Scott Donald Barnicki, Kingsport, TN (US); Daniel McNabb, Kingsport, TN (US); James Eric Ward, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 16 days.

(21) Appl. No.: 13/474,837

(22) Filed: May 18, 2012

(65) Prior Publication Data

US 2013/0310608 A1 Nov. 21, 2013

(51) Int. Cl.
C07C 45/48 (2006.01)

(52) U.S. Cl.
USPC ........................................................ 568/397

(58) Field of Classification Search
USPC ........................................................ 568/397
See application file for complete search history.

(56) References Cited

U.S. PATENT DOCUMENTS

| 1,892,742 | A | 1/1933 | Walter et al. |
| 1,926,632 | A | 9/1933 | Konstanz |
| 1,941,640 | A | 1/1934 | Tressler |
| 1,979,586 | A | 11/1934 | Tressler |
| 2,108,156 | A | 2/1938 | Wortz |
| 2,218,660 | A | 10/1940 | Schowalter et al. |
| 2,271,708 | A | 2/1942 | Neber |
| 2,457,696 | A | 12/1948 | Lukes et al. |
| 2,697,729 | A | 12/1954 | Ohlson et al. |
| 3,043,852 | A | 7/1962 | Mills |
| 3,288,853 | A | 11/1966 | Barlassina et al. |
| 3,391,191 | A | 7/1968 | Velde |
| 4,311,854 | A | 1/1982 | Weber et al. |
| 4,721,815 | A | 1/1988 | Hussmann et al. |
| 4,754,074 | A | 6/1988 | Hussmann |
| 4,929,761 | A | 5/1990 | Hussmann et al. |
| 4,950,763 | A | 8/1990 | Schommer et al. |
| 5,416,239 | A | 5/1995 | Westfechtel et al. |
| 5,475,144 | A | 12/1995 | Watson et al. |
| 5,695,575 | A | 12/1997 | Angevaare et al. |
| 6,818,796 | B2 | 11/2004 | Jacquot |
| 7,452,841 | B2 | 11/2008 | Ignatchenko et al. |
| 7,456,326 | B2 | 11/2008 | Howard |
| 7,501,379 | B2 | 3/2009 | Ignatchenko et al. |
| 7,659,432 | B2 | 2/2010 | Ignatchenko et al. |
| 8,053,614 | B2 | 11/2011 | Aalto et al. |
| 8,148,579 | B2 | 4/2012 | Bradin |
| 2004/0054234 | A1 | 3/2004 | Jacquot |
| 2007/0012233 | A1 | 1/2007 | Zhu et al. |
| 2007/0088180 | A1 | 4/2007 | Ignatchenko et al. |
| 2007/0088181 | A1 | 4/2007 | Ignatchenko et al. |
| 2007/0093679 | A1 | 4/2007 | Ignatchenko et al. |
| 2007/0100166 | A1 | 5/2007 | Beavers et al. |
| 2008/0014537 | A1 | 1/2008 | Atreya |
| 2008/0302001 | A1 | 12/2008 | Koivusalmi et al. |
| 2009/0014354 | A1 | 1/2009 | Knuuttila et al. |
| 2009/0182173 | A1 | 7/2009 | Ignatchenko et al. |
| 2010/0113735 | A1 | 5/2010 | Fogle, III et al. |
| 2010/0113824 | A1 | 5/2010 | Fogle, III et al. |
| 2010/0113826 | A1 | 5/2010 | Fogle, III et al. |
| 2010/0324310 | A1 | 12/2010 | Dumesic et al. |
| 2011/0100007 | A1 | 5/2011 | Carrick et al. |
| 2011/0185628 | A1 | 8/2011 | Johnston et al. |

FOREIGN PATENT DOCUMENTS

| CA | 262932 A | 7/1926 |
| CA | 266538 A | 12/1926 |
| CA | 389883 A | 7/1940 |
| CA | 474782 A | 6/1951 |
| CA | 490471 A | 2/1953 |
| CA | 713110 A | 7/1965 |
| CA | 2 688 449 A1 | 12/2008 |
| DE | 55651 | 5/1905 |
| DE | 2758113 A1 | 7/1979 |
| GB | 134144 | 10/1919 |
| GB | 1208802 | 10/1970 |
| WO | 2007038370 A1 | 4/2007 |
| WO | WO 2011/097217 A2 | 8/2011 |

OTHER PUBLICATIONS

International Search Report and Written Opinion with Mailing Date of Aug. 2, 2012 for International Application No. PCT/US2013/040267.
Walas, Stanley M., "Chemical Process Equipment, Selection and Design," Butterworth Publishing, 1988, pp. 211-214.
Pestman, R., et al., "Reactions of Carboxylic Acids on Oxides," Journal of Catalysts 168, 265-272 (1997), Article No. CA971624.
Fleisher, M., et al., "Theoretical study of the ketonization reaction mechanism of acetic acid over $SiO_2$," 13rd International Electronic conference on Synthetic Chemistry (ECSOC-13), Nov. 1-30, 2009. http://www.mdpi.org/ecsoc-13/ and http://www.usc.es/congresos/ecsoc/13/.
Rentz, Michael, "Ketonization of Carboxylic Acids by Decarboxylation: Mechanism and Scope," Eur. J. Org. Chem. 2005, 979-988.
Hendren, Travis S., et al., "Kinetics of catalyzed acid/acid and acid/aldehyde condensation reactions to non-symmetric ketones," Catalysis Today 85 (2003) 333-351.
Gangadharan, Anirudhan, et al., "Condensation reactions of propanal over $Ce_xZr_{1-x}O_2$ mixed oxide catalysts," Applied Catalysis a: General 385 (2010) 80-91.
Glinski, M., et al., "Ketones from monocarboxylic acids: Catalytic ketonization over oxide systems," Applied Catalysis A: General 128 (1995) 209-217.

(Continued)

Primary Examiner — Sikarl Witherspoon
(74) Attorney, Agent, or Firm — Eric D. Middlemas

(57) ABSTRACT

Disclosed is a process for reducing the emission of volatile organic compounds that are produced during the ketonization of carboxylic acids to ketones. The ketonization of carboxylic acids produces a gaseous by-product stream containing carbon dioxide and volatile organic compounds. This gaseous by-product stream can be fed to a direct-fired furnace used to heat the ketonization reaction feed streams where the volatile organic compounds are destroyed by combustion in the furnace. The carbon dioxide stream further acts as a diluent for the fuel to the furnace.

21 Claims, 1 Drawing Sheet

(56) References Cited

OTHER PUBLICATIONS

Hasan, M.A., et al., "Oxide-catalyzed conversion of acetic acid into acetone: an FTIR spectroscopic investigation," Applied Catalysis A: General 243 (2003) 81-92.

Dooley, Kerry M., et al., "Ketones from acid condensation using supported $CeO_2$ catalysts: Effect of additives," Applied Catalysis A: General 320 (2007) 122-133.

Yamada, Yasuhiro, et al., "Catalytic performance of rare earth oxides in ketonization of acetic acid," Journal of Molecular Catalysis A: Chemical 346 (2011) 79-86.

Murkute, Ambareesh D., et al., "Supported mesoporous solid base catalysts for condensation of carboxylic acids," Journal of Catalysis 278 (2011) 189-199.

Busca, Guido, et al., "FT-IR Study of the Surface Properties of $K_2O$—$TiO_2$," Applied Surface Science 27 (1986) 114-126.

Klimkiewicz, R., et al., "Application of Zr—Mg—Y—O Catalyst for Ketonization of Ester and Alcohol Type Industrial Wastes," Polish Journal of Environmental Studies vol. 12, No. 1 (2003), 67-71.

Kim, K.S., et al., "Structure and Composition Requirements for Deoxygenation, Dehydration, and Ketonization Reactions of Carboxylic Acids on $TiO_2$(001) Single-Crystal Surfaces," Journal of Catalysis 125, 353-375 (1990).

Kim, K.S., et al., "Pathways for Carboxylic Acid Decomposition on $TiO_2$," Langmuir 1988, 4, 945-953.

Nagashima, Osamu, et al., "Ketonization of carboxylic acids over CeO2-based composite oxides," Journal of Molecular Catalysis A: Chemical 227 (2005) 231-239.

Simmie, John M., "Detailed chemical kinetic models for the combustion of hydrocarbon fuels," Progress in Energy and Combustion Science 29 (2003) 599-634.

Jayamani, M., et al., "Reaction of Carboxylic Acids with Carbonyl Compounds over Alumina," Journal of Catalysis 87, 93-97 (1984).

Klimkiewicz, Roman, et al., "Zastosowanie Heterogenicznego Katalizatora Do Ketonizacji Odpadowych Kwasow Monokarboksylowych $C_4$—$C_6$," Prace Naukowe Akademii Ekonomicznej We Wroclawiu Nr 1041, 2004.

Stubenrauch, J., et al., "Reaction of carboxylic acids on $CeO_2$(111) and $CeO_2$(100)," Catalysis Today 28 (1996) 431-441.

Gürbüz, Elif I., et al., "Dual-bed catalyst system for C-C coupling of biomass-derived oxygenated hydrocarbons to fuel-grade compounds," Green Chem., 2012, 12, 223-227, Published on Jan. 13, 2010 on http://pubs.rsc.org|doi:10.1039/B920369A.

Gaertner, Christian A., et al., "Ketonization Reactions of Carboxylic Acids and Esters over Ceria-Zirconia as Biomass-Upgrading Processes," Ind. Eng. Chem. Res. 2010, 49, 6027-6033.

Gaertner, Christian A., et al., "Catalytic coupling of carboxylic acids by ketonization as a processing step in biomass conversion," Journal of Catalysis 266 (2009) 71-78.

Gürbüz, Elif I., et al., "Integration of C-C coupling reactions of biomass-derived oxygenates to fuel-grade compounds," Applied Catalysis B: Environmental, vol. 94, Issues 1-2, Feb. 1, 2012, pp. 134-141.

Peters, Jonathan E., et al., "Direct Coupled Catalytic Upgrading of Switchgrass Pyrolysis Bio-oil Vapors," Prep. Pap.-Am. Chem. Soc., Div. Petr. Chem. 2010, 55 (2), 101-103.

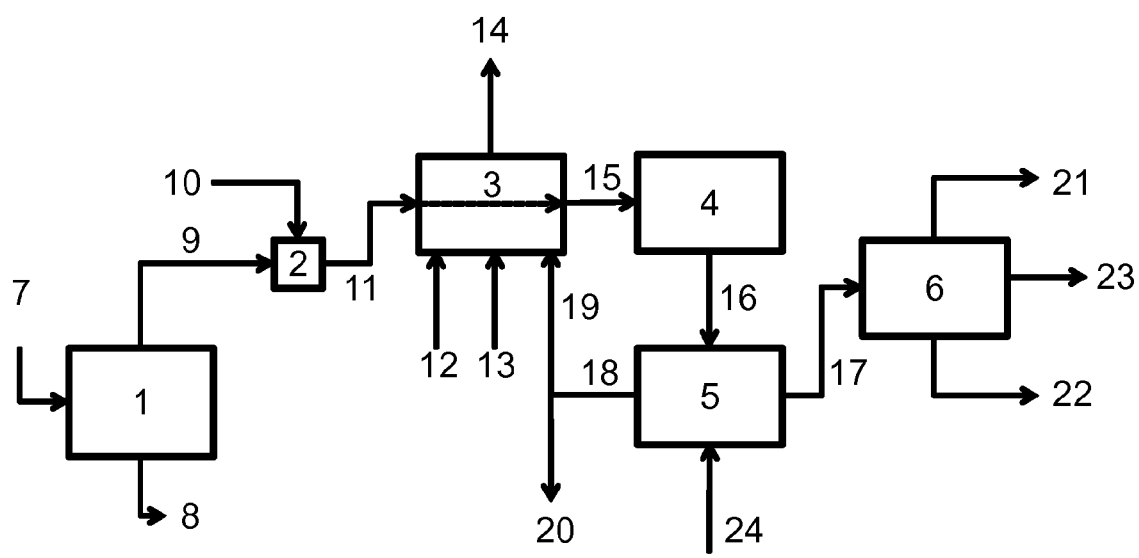

PROCESS FOR REDUCING EMISSIONS OF VOLATILE ORGANIC COMPOUNDS FROM THE KETONIZATION OF CARBOXYLIC ACIDS

FIELD OF THE INVENTION

This invention pertains to a process for reducing the emission of volatile organic compounds from gaseous by-product streams produced by the ketonization of carboxylic acids. More particularly, the invention pertains to a ketonization process in which the emission of volatile organic compounds is reduced by feeding a by-product stream containing carbon dioxide and volatile organic compounds to a direct-fired furnace that is used to heat the ketonization feed streams. The volatile organic compounds are destroyed in the direct-fired furnace.

BACKGROUND OF THE INVENTION

The ketonization of carboxylic acids is a useful method for the production of dialkyl ketones. For example, the ketonization of acetic acid alone or with other carboxylic acids, esters, and aldehydes is a valuable and high yield method for the production of acetone and other methyl ketones. The ketonization process, however, produces a number of by-products, including a substantial volume of carbon dioxide and smaller amounts of volatile organic compounds (referred to herein as "VOC's") such as, for example, various olefins, hydrogen, and methane. Emission of these VOC's with the carbon dioxide by-product stream is undesirable from an environmental standpoint. The recovery or destruction of VOC's by absorption/distillation, catalytic combustion, fuel-supplemented incineration, or the like, however, is costly and capital-intensive. An inexpensive method for capturing and reducing the emission of VOC's produced by the ketonization process, therefore, would lessen its environmental impact and improve its usefulness as a means for the production of dialkyl ketones.

SUMMARY OF THE INVENTION

Volatile organic compounds produced during the ketonization of carboxylic acids may be efficiently and inexpensively destroyed by feeding the by-product carbon dioxide stream containing these VOC's to a direct-fired furnace that is used to heat the ketonization feeds. One embodiment of our invention, therefore, is a process for reducing the emission of volatile organic compounds from a ketonization process, comprising:

(i). heating a vaporized feed stream comprising one or more carboxylic acids in a direct-fired furnace comprising a combustion zone to produce a superheated feed stream;
(ii). contacting the superheated feed stream with a metal oxide catalyst to form a gaseous product mixture comprising one or more ketones, carbon dioxide, and one or more volatile organic compound by-products;
(iii). separating the one or more ketones from the carbon dioxide and one or more volatile organic compound by-products; and
(iv). feeding at least a portion of the carbon dioxide and the one or more volatile organic compound by-products to the combustion zone of the direct-fired furnace.

The VOC's contained within the carbon dioxide gas stream are at least partially destroyed by combustion within the direct-fired furnace. Thus, no additional costly unit operations must be employed specifically for destruction of the VOC's. In addition, because the carbon dioxide in the by-product stream acts as a diluent for the fuel to the furnace, our process also moderates temperature within the furnace and reduces coking within the ketonization reactor.

The process of the invention may be used with carboxylic acids having from 2 to 20 carbon atoms including, but not limited to, acetic acid, propionic acid, butyric acid, isobutyric acid, valeric acid, hexanoic acid, heptanoic acid, octanoic acid, 2-ethyl hexanoic acid, nonanoic acid, or mixtures thereof. Although many different carboxylic acids may be the used as feedstocks, the invention is particularly useful for the production of acetone by the ketonization of acetic acid in the presence of metal oxide catalysts followed by absorption of the crude vapor into an absorption solvent. Another embodiment of the invention, therefore, is a process for reducing the emission of volatile organic compounds from the production of acetone, comprising:

(i). heating a vaporized feed stream comprising acetic acid in a direct-fired furnace comprising a combustion zone to produce a superheated feed stream having a temperature of about 350 to about 550° C.;
(ii). contacting the superheated feed stream with a catalyst comprising one or more metal oxides of titanium, zirconium, lanthanum, cerium, thorium, or mixtures thereof to produce a gaseous product mixture comprising carbon dioxide, acetone, and one or more volatile organic compound by-products;
(iii). contacting the gaseous product mixture with an absorption solvent to produce a crude liquid absorbent stream comprising a major portion of the acetone in the gaseous product mixture and a gaseous by-product stream comprising carbon dioxide, a minor portion of the acetone in the gaseous product mixture, and the one or more volatile organic compound by-products; and
(iv). feeding a least a portion of the gaseous by-product stream to the combustion zone of the direct-fired furnace, wherein the combustion zone contains sufficient oxygen for complete combustion of the acetone and the one or more volatile organic compound by-products present in the gaseous by-product stream fed to the combustion zone.

The acetone from our ketonization process can be recovered by absorption into water and distillation of the resulting aqueous absorbent stream. Accordingly, another embodiment of the invention is a process for the preparation of acetone, comprising (i). heating a vaporized feed stream comprising acetic acid in a direct-fired furnace comprising a combustion zone to produce a superheated feed stream having a temperature of about 350 to about 650° C.;
(ii). contacting the superheated feed stream with a catalyst comprising one or more metal oxides to produce a gaseous product mixture comprising carbon dioxide, acetone, and one or more volatile organic compound by-products;
(iii). contacting the gaseous product mixture with water to produce a liquid absorbent stream comprising a major portion of acetone in the gaseous product mixture and a gaseous by-product stream comprising carbon dioxide, a minor portion of the acetone in the gaseous product mixture, and the one or more volatile organic compound by-products;
(iv). feeding a least a portion of the gaseous by-product stream to the combustion zone of step (i); and
(v). distilling the liquid absorbent stream to produce a distillate comprising a refined acetone product and a distillation bottoms comprising water.

BRIEF DESCRIPTION OF THE DRAWINGS

FIG. 1 is a schematic flow diagram of a ketonization process that illustrates one embodiment of the invention.

DETAILED DESCRIPTION

The present invention provides a process for reducing the emission of volatile organic compounds produced as by-products in the ketonization of carboxylic acids to form ketones. In a general embodiment, the process of our invention comprises:

(i). heating a vaporized feed stream comprising one or more carboxylic acids in a direct-fired furnace comprising a combustion zone to produce a superheated feed stream;

(ii). contacting the superheated feed stream with a metal oxide catalyst to form a gaseous product mixture comprising one or more ketones, carbon dioxide, and one or more volatile organic compound by-products;

(iii). separating the one or more ketones from the carbon dioxide and one or more volatile organic compound by-products; and (iv). feeding at least a portion of the carbon dioxide and the one or more volatile organic compound by-products to the combustion zone of the direct-fired furnace.

The VOC by-products can be efficiently and inexpensively destroyed by feeding a gaseous by-product stream from the ketonization reaction comprising carbon dioxide and the VOC by-products to a direct-fired reactor feed superheater furnace. Such furnaces typically are required to heat the feed streams to the high temperatures required for the ketonization reaction. The carbon dioxide present in the by-product stream also functions as a temperature-moderating diluent with the fuel and air components fed to the direct-fired reactor feed furnace. In the furnace, the VOC's are burned with the fuel component to superheat the acid feed to the ketonization reactor. Combustion of at least 50% of the inlet VOC's may be achieved in such a manner. Our process, therefore, requires no additional costly unit operations specifically for destruction of the VOC's.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the appended claims, the singular forms "a," "an" and "the" include their plural referents unless the context clearly dictates otherwise. For example, references to a "furnace," or a "compound," are intended to include one or more furnaces or compounds. References to a composition or process containing or including "an" ingredient or "a" step are intended to include other ingredients or other steps, respectively, in addition to the one named.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

The ketonization of carboxylic acids is well-known method for the production symmetrical and unsymmetrical ketones. The term "ketonization," as used herein, is intended to be synonymous with the term "ketonic decarboxylation," and refers to a process in which ketone is formed from the decarboxylative condensation of two carboxylic acid molecules. Symmetrical ketones are produced from a single carboxylic acid. When two different carboxylic acids are used as starting materials, a mixture of the symmetrical ketones from each carboxylic acid is produced together with an unsymmetrical ketone from the coupling of the different carboxylic acids. Although the process of invention may be used with any carboxylic acid, it can be illustrated with particular reference to the ketonization of acetic acid with itself and the cross ketonization of acetic acid with higher carboxylic acids to produce acetone and higher molecular weight methyl ketones. The general reactions for self- and cross-ketonization of acetic acid may be illustrated with the following reaction schemes (I) and (II) shown below:

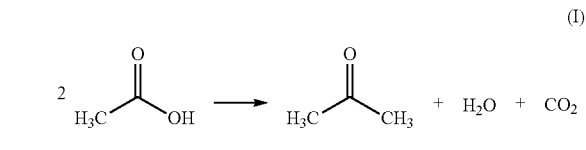

(I)

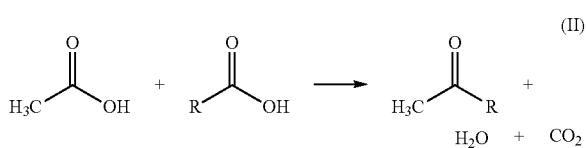

(II)

Unsymmetrical methyl ketones may be produced by cofeeding other carboxylic acid with acetic acid. For example, cofeeding propionic acid with acetic acid results in the formation of methyl ethyl ketone; n-butyric acid with acetic acid results in the formation of methyl propyl ketone; and the reaction of isobutyric acid with acetic acid results in formation of methyl isopropyl ketone. In addition to the ketone products, the ketonization reaction produces 1 mole of carbon dioxide and 1 mole of water per mole of ketone product.

The product ketones, as exemplified and illustrated by acetone derived via ketonization of acetic acid in a manner described above, may undergo further reaction over the ketonization catalyst to form higher α,β-unsaturated ketones by an aldol-like condensation and dehydration. For example, mesityl oxide may be formed by condensation of acetone. These unsaturated ketones may be further converted into various olefins. For example, mesityl oxide may undergo a further decomposition reaction to produce a reaction product comprising isobutylene. Although the formation of isobutylene represents a relatively minor yield loss (typically about 0.02 to about 0.8 mole percent conversion of the acetic acid feed to isobutylene), isobutylene is a highly volatile species and is difficult to remove from the effluent carbon dioxide by-product stream in a cost effective manner. Moreover, the effluent by-product carbon dioxide stream may contain small amounts of unrecovered product ketone such as, for example, acetone, and other by-products resulting from side reactions, exemplified by methane, hydrogen, mesitylene, isophorone, and mixtures thereof, or by reactions of feed impurities with acetic acid, as exemplified by methyl ethyl ketone (via ketonization of acetic acid with traces of propionic acid). It is also undesirable to release these compounds to the environment with the by-product carbon dioxide stream.

The process of the invention includes heating a vaporized feed stream comprising one or more carboxylic acids in a direct-fired furnace comprising a combustion zone to produce a superheated feed stream. The carboxylic acids can comprise straight or branched-chain carboxylic acids having from 2 to 20 carbon atoms. For example, the vaporized feed stream can comprise one or more straight or branched-chain carboxylic acids containing 2 to 10 carbon atoms. Some examples of carboxylic acids that can be used as reactants for our novel process include, but are not limited to, acetic acid, propionic acid, butyric acid, isobutyric acid, valeric acid, hexanoic acid, octanoic acid, 2-ethylhexanoic acid, nonanoic acid, or mixtures thereof. In another embodiment, the one or more carboxylic acids can comprise acetic acid.

Our invention may be described and illustrated with particular reference to the ketonization of acid feed streams in which the carboxylic acid comprises acetic acid. It will be apparent to persons having ordinary skill in the art, however, that the various embodiments of the process described herein can be carried out as described or with minor modifications using higher molecular weight carboxylic acids having 2 to 20 carbon atoms as described above. The vaporized feed stream will typically comprise about 20 to 100 weight percent of the carboxylic acid and 0 to about 10 weight percent of a carboxylic acid anhydride, based on the total weight of the vaporized feed stream. For example, the vaporized stream may comprise acetic acid and acetic anhydride in the above concentrations. Because of excessive fouling of the vaporizer, superheater, and reactor, it is often undesirable to feed anhydrous acid or anhydride. To avoid excessive fouling of the process equipment, therefore, the vaporized feed stream may be mixed with sufficient water to hydrolyze any carboxylic acid anhydrides that may be present. Additional water may be added prior to vaporization or may be already present in the original acid stream to give a final concentration of water in the acid feed stream of greater than 0 weight percent to about 70 weight percent, based on the total weight of the vaporized feed stream. In another example, the vaporized feed stream can contain greater than 0 percent to about 20 weight percent water.

Typically, the feed stream containing the carboxylic acid may be vaporized at a temperature of about 110 to about 350° C., depending on the molecular weight of the carboxylic acid, and at a pressure of about 0.7 to about 7 bar absolute. For example, an acid feed stream comprising acetic acid can be vaporized at a temperature of about 110 to about 195° C. at a pressure of about 0.7 to about 7 bar absolute. In another example, the feed stream containing acetic acid can be vaporized at a temperature of about 115 to about 160° C. at a pressure of about 0.9 to about 3.2 bar absolute. The vaporizer can be any apparatus known to persons skilled in the art such as, for example, kettle-type, thermosyphon-type, wiped-film, falling film, and thin film evaporators. Typically 1.0 to 25.0% of the incoming wet acid stream can be removed as a sludge stream from the vaporizer to prevent fouling of the vaporizer equipment, the furnace superheater, and the catalyst bed, as well as to remove non-volatile components such as salts and tars. Optionally, steam may be added to the vaporized acid to bring the water concentration in the wet acid stream to about 5 to about 70 weight percent water, or in another example, about 10 to about 20 weight percent water, based on the total weight of the vaporized wet acid stream. The addition of water to the vaporized feed stream helps to reduce coke formation in the ketonization reactor.

The wet acid feed is heated in a direct-fired furnace that comprises a combustion zone to produce a superheated feed stream. The term "superheated," as used herein, is intended to have its commonly understood meaning of a vapor heated to a temperature above its dew point at a given pressure. The term "superheater," as used herein, refers to the direct-fired furnace used to superheat the feed stream for the ketonization reaction. The temperature of the superheated feed stream is typically about 350 to about 650° C. In another example, the temperature of the superheated feed stream can be about 350 to about 600° C. In still another example, the temperature of the superheated feed stream can be about 350 to about 550° C. Any direct-fired furnace or heater known to persons having ordinary skill in the art may be used in which heat is released by combustion of fuels into an open space and transferred to fluids inside tubes which are ranged along the walls and roof of the combustion chamber. The heat released from the combustion of fuels can be transferred by direct radiation, convection, and reflection from refractory walls lining the chamber. For example, the wet acid feed may be conveyed through the superheater via a multi-pass tubular configuration inside of an insulated furnace box in which a fuel is combusted with oxygen and diluent to generate high temperature heat. Although any conventional source of oxygen can be used, air is generally the least expensive and most readily available source of oxygen.

The combustion zone of the direct-fired furnace can comprise radiative and convective heating sections wherein heat may be transferred to the tubes containing the vaporized feed via radiative and convective heat transfer mechanisms. In the radiative zone, heat transfer is predominantly by radiation, typically about 90% from radiation. Since radiative heat transfer varies by the $4^{th}$ power of temperature, the radiative section is the hottest part of the furnace and is close to the burners. In the convective section the majority of heat transfer occurs through convective, i.e., flow, mechanisms, although some radiative heat transfer may occur. A transition region, called the shield zone in the art, occurs where convective and radiative heat transfer contributions are about equal. The shield zone typically occurs when the combustion product gases have cooled to 700 to 900° C., and are at least 90° C. above the process temperature at this point. For the purposes of this invention, the convective section is considered to be any section of the direct-fired furnace wherein radiative heat transfer comprises 50% or less of the heat transfer occurring in the furnace zone. Methods for determining the amount of radiative heat transfer in a furnace section are well-known in the art and are described, for example, in Walas, S. *Chemical Process Equipment*. Butterworth Publishing, 1988, pp. 212-214. In one embodiment of the invention, the majority of heat transfer can occur in a convective section of the furnace in which sufficient diluent has been added to the already combusted hot fuel and air mixture to lower its temperature to 700 to 900° C. The reduction of temperature in the convective section of the furnace by the addition of a diluent can help to prevent high tube skin temperatures and coking on the vaporized feed side of the tubes. The diluent gas may be air or carbon dioxide obtained as a by-product of the ketonization reaction, or a combination of both. For example, in one embodiment of the invention, the diluent gas comprises the by-product carbon dioxide stream from the ketonization reaction in addition to any excess air required for combustion. In this context, excess air refers to the oxygen, typically as a constituent of air, supplied above the stoichiometric amount of oxygen required for combustion of all oxidizable fuel components fed to the furnace. Generally, about 10 to about 40 percent excess air may be fed to the direct-fired furnace to ensure essentially complete combustion of fuel components.

The air feed may be supplied to the combustion zone of the furnace by natural or forced draft. Typically, sufficient air is supplied to give 10 to 40% excess oxygen over the stoichiometric amount required for complete combustion of both the fuel and the VOC components in the by-product carbon dioxide stream. The direct-fired furnace can be sized to supply sufficient heat to raise the wet acid feed to the proper reaction temperature by providing both sensible heat and sufficient thermal energy to compensate for the endothermic heat of ketonization. Typically, the furnace may be designed to supply about 0.7 to about 2.6 million J/kg of carboxylic acid fed to the ketonization reactor and will depend strongly on the water content of the vaporized acid stream. In another example, the furnace can be designed to supply about 0.75 to about 0.9 million J/kg of carboxylic acid fed to the furnace.

The fuel for the furnace may be any combustible material of sufficient energy density including, but not limited to, natural gas, propane, butane, natural gas liquids, liquefied petroleum gases, hydrogen, refinery off-gases, pyrolysis gasoline, ethanol, methanol, heavy organic by-products from the ketonization reactor, such as mesityl oxide and related compounds, the sludge stream from the acid vaporizer, or petroleum fractions, such as gasoline, kerosene, bunker fuel, heating oil, and the like. The design and configuration of the direct-fired furnace burners is highly dependent on the type of fuel chosen and is well known to persons skilled in the art. In one embodiment, for example, natural gas may be used as the furnace fuel.

The direct-fired furnace as described above may be employed for ketonization reactions conducted in an adiabatic or an isothermal mode. In an adiabatic mode of operation, the superheated acid feed stream is passed to a ketonization reactor positioned outside of the furnace box where the reaction occurs without additional heating from the furnace. In an isothermal mode, by contrast, the furnace process tubes are filled with ketonization catalyst and reaction occurs simultaneously with direct-fired heating.

The superheated feed stream is passed to ketonization reactor wherein it is contacted with a metal oxide catalyst to form a gaseous product mixture comprising one or more ketones, water, carbon dioxide, and one or more volatile organic compounds ("VOC's"). The term "volatile organic compound," as used in the context of the present description and claims, is intended to mean an organic compound having a boiling point less than or equal to 250° C. measured at a standard atmospheric pressure of 101.3 kPa. The term VOC, as referred to herein, can include any organic compounds which have been determined to have negligible photochemical reactivity. Some examples of VOC's include, but are not limited to, methane, ethane, methylene chloride (dichloromethane), 1,1,1-trichloroethane (methyl chloroform), 1,1,2-trichloro-1,2,2-trifluoroethane (CFC-113), trichlorofluoromethane (CFC-11), cyclic, branched, or linear completely methylated siloxanes, acetone, methyl acetate, dimethyl carbonate, propylene carbonate, isobutylene, mesityl oxide, terpenes, methyl ethyl ketone, isophorone, and other low molecular weight aldehydes, ketones, hydrocarbons, olefins, alcohols, and esters.

VOC's can contribute to smog and other forms of atmospheric pollution and their emission into the atmosphere is restricted for environmental reasons. As noted above, some examples of volatile organic compounds produced by the ketonization of acetic acid include, but are not limited to, isobutylene, methane, mesityl oxide, isophorone, and mixtures thereof.

The ketonization reaction is typically carried out in the gas phase and can be catalyzed by a number of metal oxides such as, for example, the oxides of rare earth metals, transition metals, alkali metals, and alkaline earth metals. The metal oxide catalysts can exhibit both acid and base functionalities. The metal oxides may be employed either alone or in combination with one or more metals. Representative examples of metal oxide ketonization catalysts may be found in Glinski et al, "Ketones from Monocarboxylic Acids: Catalytic Ketonization Over Oxide Catalysts", *Applied Catalysis A: General*, Vol. 128, (1995) pp. 209-217. The metal oxides may be supported on inorganic carriers well-known to persons skilled in the art such as, for example, silica, titania, or alumina. The activity and selectivity of the metal oxide catalyst may be enhanced by the presence of metal oxides of the Group IA metals, such as lithium, sodium, potassium, and cesium as disclosed, for example, by U.S. Pat. No. 4,950,763.

Some specific examples of metal oxide ketonization catalysts include, but are not limited to, oxides of cerium, thorium, lanthanum, manganese, zirconium, titanium, zinc, chromium, lead, iron, niobium, molybdenum, bismuth, cadmium, copper, nickel, magnesium, aluminum, and mixtures thereof. For example, in one embodiment of the invention, the superheated feed stream has a temperature of about 350 to about 650° C. and the metal oxide catalyst comprises an oxide of titanium, zirconium, thorium, cerium, lanthanum, or a mixture thereof. The metal oxide catalyst may be further impregnated with about 0.05 to about 50 weight percent, based on the total weight of the catalyst, of lithium, sodium, potassium, cesium, lanthanum, cerium, or a combination thereof. In yet another example, the ketonization catalyst can comprise about 0.05 to about 50 weight percent, based on the total weight of the catalyst, of lithium, sodium, potassium, cesium, or a mixture thereof. In still another example, the ketonization catalyst comprises titanium dioxide impregnated with about 1 to about 10 weight percent lithium, sodium, cesium, or potassium. The titanium dioxide can be in the anatase form.

The surface area of the ketonization catalyst can range from about 10 to about 400 $m^2/g$ of catalyst. Other examples of catalyst surface areas are about 20 to about 200 $m^2/g$ and about 50 to about 200 $m^2/g$. The impregnated and/or supported catalysts can be prepared in accordance with methods well-known to persons skilled in the art such as, for example, by thoroughly mixing metal salt solutions of the catalyst and optional catalyst promoter with the carrier or support material, followed by drying and calcination of the catalyst particles. The catalyst may be in any of the commonly used catalyst shapes such as, for example, spheres, granules, pellets, chips, rings, extrudates, or powders that are well-known in the art. The ketonization catalyst can be regenerated by heating in the presence of an oxygen-containing gas at about 375 to about 550° C.

The ketonization reactor can be any reactor format known in the art to be suitable for gas-phase endothermic reactions. For example, the ketonization reaction may be conducted using a fixed, fluidized, or moving bed reactor. In another example, the ketonization reaction can be carried out in a single stage adiabatic fixed bed reactor; a multiple-stage adiabatic fixed bed reactor with interstage heating or hot-shotting; or a tubular fixed bed reactor in a fired furnace or molten salt heating bath. Because the ketonization reaction is endothermic, the reactor can be operated in an adiabatic mode. Typically about 90 to about 100% of the acetic acid will be converted to acetone, $CO_2$, and water in a single stage adiabatic reactor. The inlet pressure to the ketonization reactor typically will be from about 0.7 to about 9 bars absolute. The temperature range for the ketonization reactor can be about 300 to about 600° C. over the length of the reactor. For example, the temperature can range from about 350 to about 450° C. over the length of the reactor. When run in single stage, adiabatic mode, the reactor temperature will be highest at the inlet and drop to the lowest value at the outlet because of the endothermic heat of reaction. Typically, the temperature drop across the reactor will be about 40 to about 75° C., depending on water content of the feed and conversion of acetic acid.

In the ketonization reactor, the one or more carboxylic acids are converted into a gaseous product mixture comprising one or more ketones, carbon dioxide, and one or more volatile organic compounds. The ketone component can be separated from the carbon dioxide and one or more VOC's by conventional methods known to persons skilled in the art. For example, as illustrated by the ketonization of acetic acid to acetone, the gaseous product mixture from the ketonization reactor can be separated by direct condensation or absorption of the gaseous ketonization reactor product mixture into water to produce a condensed crude acetone stream and a vaporous carbon dioxide by-product stream comprising carbon dioxide and the volatile organic compounds such as isobutylene, hydrogen, methane, unrecovered acetone and higher ketones. In one embodiment, for example, the separation step comprises cooling the gaseous product mixture by contact with a heat exchanger or a solvent. For example, the ketone component, i.e. acetone, may be condensed by indirect cooling in a heat exchanger against water, chilled brine, chilled glycol or the like, or via direct contact cooling with an injected solvent, such as water. After cooling, phase separation produces a by-product carbon dioxide stream comprising the majority of the non-condensable components (e.g., $CO_2$, methane, isobutylene, and hydrogen), along with small amounts of acetone and higher boiling impurities; and a liquid crude acetone comprising the majority of the acetone and heavy by-products from the reactor. The temperature range of the condenser operation is 0 to 40° C., preferably 5 to 25° C. Generally recovery of acetone by condensation results in about 90% or greater recovery of acetone. Some additional examples of the amount of acetone recovery by condensation are about 95% or greater and about 99% or greater.

High recovery of acetone by condensation alone, however, requires very low temperatures because of the volatile nature of acetone and the large volume of by-product carbon dioxide present in the gaseous reactor effluent. Alternatively, acetone may be recovered from the gaseous reactor effluent by absorption into a solvent such as, for example, water. The absorption may be carried out by any means known to those skilled in the art, for example, by contacting the gaseous product mixture with water in a countercurrent absorber such as, for example, a packed or trayed absorption tower. In one embodiment of the invention, for example, the gaseous reactor effluent containing acetone can be fed to the bottom of the absorption tower and acetone-lean solvent, e.g., water, can be fed to the top of the tower, which permits the gas and liquid phases co-mingle in a countercurrent flow pattern. The acetone-lean carbon dioxide by-product stream can be removed from the top of the tower, and the acetone-rich crude acetone stream can be removed from the bottom of the column. The solvent to feed weight ratio is typically about 0.5:1 to about 3:1. In one embodiment, the absorber may be run adiabatically. The high heat of absorption of acetone, however, may require heat removal to minimize solvent flow, staging, and to enable the maximum recovery of acetone. For example, the heat of absorption may be removed by side draw coolers or by a heat-exchanged pump around loop in which liquid from the bottom effluent of the absorber is pumped through a heat exchanger and fed back into the column, typically about ¼ to about ½ of the distance from the bottom of the column to the top. The flow in the pump around loop may be about 0.5 to about 10 times the flow of the crude acetone product removed from the bottom of the absorber or, in another example, about 1 to about 4 times the flow of the crude acetone product. For example, the temperature range of absorber operation can be about 10 to about 65° C. or, in another example, about 25 to about 50° C. Any solvent with a suitable partition coefficient for acetone can be used in the absorber. Some representative examples of absorber solvents include, but are not limited to, water, $C_5$ to $C_{20}$ ketones, $C_2$ to $C_{16}$ carboxylic acids, $C_6$ to $C_{12}$ hydrocarbons, $C_6$ to $C_{16}$ ethers, $C_5$ to $C_{12}$ esters, and $C_3$ to $C_{12}$ alcohols. Some specific examples of absorber solvents are 2-pentanone, 4-methyl-2-pentaone, 2-heptanone, 5-methyl-2-hexanone, 4-heptanone, 2,4-dimethyl-5-pentanone, 2,5-dimethyl-4-heptanone, acetic acid, propionic acid, i-butyric acid, n-butyric acid, i-valeric acid, n-valeric acid, n-hexanoic acid, 2-ethyl-hexanoic acid, toluene, benzene, o-/m-/p-xylenes, diisopropyl ether, dipropylether, tertiary amyl methyl ether, Dibutyl ether, n-propyl acetate, i-propyl acetate, n-butyl acetate, i-butyl acetate, sec-butyl acetate, 2-ethylhexyl acetate, ethyl propionate, n-propyl propionate, isopropyl propionate, ethyl n-butyrate, ethyl i-butyrate, methyl 2-ethylhexanoate, isopropanol, n-propanol, sec-butanol, i-butanol, n-butanol, n-hexanol, 2-ethylhexanol, and n-decanol. In one embodiment of the invention, water can be used as the absorber solvent. Water is inexpensive, plentiful, and effective for the absorbing acetone. In addition, water is already present in the process and does not require an additional step for recovery of the solvent from the by-product carbon dioxide stream after absorptive recovery of the acetone. Generally, the recovery of acetone by countercurrent absorption into water results in about 99% or greater recovery of acetone. Some additional examples of acetone recovery from the absorber are about 99.5% or greater and about 99.8% or greater.

After separation from the ketone component of the gaseous product mixture, the carbon dioxide by-product stream will generally comprise about 95 to about 99.9 mole percent carbon dioxide, 0 to about 0.4 mole percent methane, 0 to about 0.5 mole percent hydrogen, and about 0.02 to about 0.8 mole percent isobutylene, based on the weight of the carbon dioxide by-product stream on an acetone and water free basis. In addition, the carbon dioxide by-product stream may contain unrecovered acetone, typically about 0.05 to about 5 mole percent acetone, about 0.1 to about 4 mole percent water, and 0 to about 100 ppm of other heavier by-products.

In accordance with the invention, at least a portion of the carbon dioxide by-product stream is fed to combustion zone of the direct-fired furnace, which destroys at least a portion of the volatile organic compounds by combustion to carbon dioxide. The furnace may be designed such that residence time and temperature are sufficient for the combustion of at least 50 weight percent or, in another example, at least 65 weight percent of the total VOC's present originally in the by-product carbon dioxide stream. For example, about 50 to 100 weight percent of the volatile organic compounds fed to combustion zone can be converted to carbon dioxide, based on the total weight of the volatile organic compounds fed to the combustion zone. Typically, the carbon dioxide and one or more volatile organic compound by-products are fed to the convective section of the combustion zone. In one embodiment, for example, the residence time of the VOC's in the convective section of combustion zone can be about 0.02 to about 5.0 seconds. In another example, the residence time of the VOC's in the convective section of the combustion zone can be about 0.1 to about 0.5 seconds. The temperature in the convective section of the combustion zone of the furnace will typically be about 600 to about 900° C. In another example, the temperature of the convective section of the combustion zone can be about 650 to about 800° C.

After condensation or absorption and separation of the carbon dioxide by-product step, the crude ketone stream can be distilled to produce a high purity ketone product. For example, during the ketonization of acetic acid to acetone, the crude acetone stream obtained after condensation or absorption can comprise about 25 to about 65 weight percent acetone, about 0.5 to about 2 weight percent mesityl oxide and other related by-products such as, for example, isophorone and mesitylene, about 35 to about 75 weight percent water, and about 0.05 to about 2 weight % acetic acid. This stream can be fed to a distillation column where a distillate containing about 95 to about 99 weight percent acetone, about 1 to about 5 weight percent water, and up to 500 ppm levels of reaction by-products such as, for example, mesityl oxide, may be removed from the top of the column. Water, acetic acid, and the remaining heavy reactor by-products can be removed from the bottom of the column.

As noted above, the process of the invention is useful for the production acetone by the ketonization of acetic acid. Another embodiment of our invention, therefore, is a process for reducing the emission of volatile organic compounds from the production of acetone, comprising
(i). heating a vaporized feed stream comprising acetic acid in a direct-fired furnace comprising a combustion zone to produce a superheated feed stream having a temperature of about 350 to about 550° C.;
(ii). contacting the superheated feed stream with a catalyst comprising one or more metal oxides of titanium, zirconium, lanthanum, cerium, thorium, or mixtures thereof to produce a gaseous product mixture comprising carbon dioxide, acetone, and one or more volatile organic compound by-products;
(iii). contacting the gaseous product mixture with an absorption solvent to produce a crude liquid absorbent stream comprising a major portion of the acetone in the gaseous product mixture and a gaseous by-product stream comprising carbon dioxide, a minor portion of the acetone in the gaseous product mixture, and the one or more volatile organic compound by-products; and
(iv). feeding a least a portion of the gaseous by-product stream to the combustion zone of the direct-fired furnace, wherein the combustion zone contains sufficient oxygen for complete combustion of the acetone and the one or more volatile organic compound by-products present in the gaseous by-product stream fed to the combustion zone.

It is understood that the above process can include any combination of the various embodiments of the direct-fired furnace, combustion zone, superheated feed stream, ketonization catalyst and reactor, product separation, carbon-dioxide by-product stream, volatile organic compounds, and purification of the acetone product as described hereinabove.

For example, the wherein the vaporized feed stream can comprise about 70 to about 100 weight percent acetic acid and about 0 to about 30 weight percent water. In another example, the vaporized feed stream can comprise greater than 0 percent to about 20 weight percent water. As described above, the gaseous product mixture can comprise the one or more volatile organic compound by-products such as, for example, isobutylene, methane, hydrogen, or mixtures thereof.

In order to achieve efficient combustion of the volatile organic compound by-products, the combustion zone of the direct-fired furnace can contain about 10 to about 40 mole percent excess oxygen over the amount required for complete combustion of the acetone and the one or more volatile organic compound by-products present in the gaseous by-product stream fed to the combustion zone. In one embodiment of the invention, at least 50 weight percent or, in another example, at least 65 weight percent of the total VOC's present originally in the by-product carbon dioxide stream are converted to carbon dioxide in the combustion zone. For example, about 50 to 100 weight percent of the volatile organic compounds fed to combustion zone can be converted to carbon dioxide, based on the total weight of the volatile organic compounds fed to the combustion zone. Typically, the carbon dioxide and one or more volatile organic compound by-products are fed to the convective section of the combustion zone. In another embodiment, the combustion zone comprises a radiative section and a convective section and the residence time of the one or more volatile organic compound by-products in the convective section of the combustion zone is about 0.02 to about 5 seconds.

The superheated feed stream may be contacted with a catalyst comprising one or more metal oxides of titanium, zirconium, lanthanum, cerium, thorium, or mixtures thereof to produce a gaseous product mixture comprising carbon dioxide, acetone, and one or more volatile organic compound by-products. For example, in yet another embodiment of the invention, the catalyst has a surface area of about 10 to about 400 $m^2/g$ of catalyst and can further comprise about 0.05 to about 50 weight percent lithium, sodium, calcium, potassium, cesium, or mixtures thereof, based on the total weight of the catalyst.

Our invention also includes a process for the preparation of acetone, comprising:
(i). heating a vaporized feed stream comprising acetic acid in a direct-fired furnace comprising a combustion zone to produce a superheated feed stream having a temperature of about 350 to about 650° C.;
(ii). contacting the superheated feed stream with a catalyst comprising one or more metal oxides to produce a gaseous product mixture comprising carbon dioxide, acetone, and one or more volatile organic compound by-products;
(iii). contacting the gaseous product mixture with water to produce a liquid absorbent stream comprising a major portion of the acetone in the gaseous product mixture and a gaseous by-product stream comprising carbon dioxide, a minor portion of the acetone in the gaseous product mixture, and the one or more volatile organic compound by-products;

(iv). feeding a least a portion of the gaseous by-product stream to the combustion zone of step (i); and (v). distilling the liquid absorbent stream to produce a distillate comprising a refined acetone product and a distillation bottoms comprising water.

It should be understood that the above process also includes any combination of the various embodiments of the direct-fired furnace, combustion zone, superheated feed stream, ketonization catalyst and reactor, product separation, carbon-dioxide by-product stream, volatile organic compounds, and purification of acetone product described hereinabove. For example, as described previously, the superheated feed stream may be contacted with one or more metal oxide catalysts in a single or multiple stage adiabatic fixed bed reactor having a temperature of about 300 to about 600° C. over the length of the reactor and an inlet pressure of about 0.7 to about 9 bars absolute. The catalyst can comprise, for example, one or more metal oxides of titanium, zirconium, cerium, thorium, lanthanum, or mixtures thereof, and can have a surface area of about 50 to about 200 $m^2/g$.

The gaseous product mixture from the ketonization reaction, comprising carbon dioxide, acetone, and one or more volatile organic compounds, is contacted with water in an absorber to produce a liquid absorbent stream comprising a major portion of acetone in the gaseous product mixture and a gaseous by-product stream comprising carbon dioxide, a minor portion of the acetone in the gaseous product mixture, and the one or more volatile organic compound by-products. In one example, the weight to weight ratio of gaseous product mixture contacted with water is about 0.5:1 to about 3:1. The resulting liquid absorbent stream can comprise about 20 to about 65 weight percent acetone, based on the total weight of the liquid absorbent stream, about 35 to about 75 weight percent water, 0 to about 3 weight percent acetic acid, and about 0.1 to about 2 weight percent mesityl oxide, isophorone, mesitylene, or a mixture thereof. The absorber can comprise any combination of the embodiments described previously; for example, the absorber can comprise a pump around loop in which the flow can be about 0.5 to about 10 times the flow of the crude acetone product removed from the bottom of the absorber or, in another example, about 1 to about 4 times the flow of the crude acetone product. In yet another example, the temperature range of absorber operation is about 10 to about 65° C. or, in still another example, about 25 to about 50° C.

The liquid absorbent stream can be distilled as described previously to produce a distillate comprising a refined acetone product and a distillation bottoms comprising water. The refined acetone product typically will comprise about 95 to 100 weight percent acetone and 0 to about 5 weight percent water, based on the total weight of the refined acetone product.

The process of the invention can be illustrated with particular reference to the simplified block flow diagram shown FIG. 1, which exemplifies one embodiment of the instant invention in which acetic acid is converted to acetone. An acetic acid feed stream is conveyed via conduit 7 to vaporization unit 1, wherein a fraction, typically 75 to 99%, of the feed is vaporized by boiling against steam, to produce vaporized acid stream 9. Typically, the acid feed stream 7 is vaporized at a temperature range of about 110 to about 195° C. and a pressure of about 0.7 to about 7.0 bars absolute. The portion of the feed acid that is not vaporized is removed from the vaporization unit as sludge stream 8. Vaporized acid stream 9 is optionally mixed at point 2 with steam stream 10 for further dilution of the feed acid to produce wet acid stream 11. The water concentration in the wet acid stream 11 can be about 5 to about 70 weight percent water, based on the total weight of stream 11. This water addition helps mitigate coke formation in the ketonization reactor.

Wet acid stream 11 is further superheated to the desired reaction inlet temperature in the direct-fired furnace 3 to produce superheated feed stream 15. Heat is provided to the furnace by combustion of fuel 12 with air stream 13, and can be diluted for temperature control by at least a portion of by-product carbon dioxide stream 18 via conduit 19. The superheated feed stream 15 is passed through ketonization reactor 4, wherein the acetic acid and other reactive feed molecules, if present, are converted over a heterogeneous ketonization catalyst to a mixture comprising acetone, water, carbon dioxide, unreacted acetic acid, and other VOC by-products to produce reactor effluent 16. Gaseous reactor effluent 16, is cooled and separated in recovery zone 5 to produce crude acetone stream 17, comprising the majority of the acetone, water, and heavy by-products; and by-product carbon dioxide stream 18 comprising carbon dioxide, isobutylene, methane, hydrogen, other minor VOC's, and traces of acetone and higher by-products. In recovery zone 5, the gaseous reactor effluent from the ketonization reactor can be condensed by indirect cooling in a heat exchanger against water, chilled brine, chilled glycol or the like, or by direct contact cooling with an injected solvent, such as water. By-product carbon dioxide stream 18, may be sent in its entirety via conduit 19 to furnace 3. Alternatively, a portion of stream 18 can be emitted directly via conduit 20. Typically during, normal operation all of stream 18 will be sent to furnace 3 for combustion of VOC's, although at start up, or during furnace upsets, a fraction or all of stream 18 may exit the process via stream 20 without further treatment. The crude acetone stream 17, comprising about 25 to about 65 weight percent acetone, about 0.5 to about 2 weight percent mesityl oxide and other related byproducts such as isophorone and mesitylene, about 35 to about 75 weight percent water, and about 0.05 to about 2 weight % acetic acid, is further purified in distillation zone 6 to produce a purified acetone stream 21, a waste water stream 22, comprising water from the acid feed 7, any added steam from conduit 10, water created in the ketonization reactor, as well as any optional absorber water stream 24; and a waste organic stream 23, comprising by-product organics produced in the ketonization reactor, or non-ketonizable species brought in as impurities in the acid feed stream 7.

The invention also includes the following embodiments 1-21 set forth below. Embodiment 1 is a process for reducing the emission of volatile organic compounds from a ketonization process, comprising:

(i). heating a vaporized feed stream comprising one or more carboxylic acids in a direct-fired furnace comprising a combustion zone to produce a superheated feed stream;

(ii). contacting the superheated feed stream with a metal oxide catalyst to form a gaseous product mixture comprising one or more ketones, carbon dioxide, and one or more volatile organic compound by-products;

(iii). separating the one or more ketones from the carbon dioxide and one or more volatile organic compound by-products; and (iv). feeding at least a portion of the carbon dioxide and the one or more volatile organic compound by-products to the combustion zone of the direct-fired furnace.

Embodiment 2 is a process that includes the features of embodiment 1, in which the one or more carboxylic acids comprise a carboxylic acid having 2 to 20 carbon atoms.

Embodiment 3 is a process that includes the features of any one of embodiments 1 and 2, in which the one or more carboxylic acids comprise acetic acid, propionic acid, butyric acid, isobutyric acid, valeric acid, hexanoic acid, heptanoic acid, octanoic acid, 2-ethyl hexanoic acid, nonanoic acid, or a mixture thereof.

Embodiment 4 is a process that includes the features of any one of embodiments 1-3, in which the one or more carboxylic acids comprise acetic acid, the one or more ketones comprise acetone, and the one or more volatile organic compound by-products comprise isobutylene, methane, hydrogen, or mixtures thereof.

Embodiment 5 is a process that includes the features of any one of embodiments 1-4, in which step (ii) is carried out in fixed bed, adiabatic reactor.

Embodiment 6 is a process that includes the features of any one of embodiments 1-5, in which the superheated feed stream has a temperature of about 350 to about 650° C. and the metal oxide catalyst comprises an oxide of titanium, zirconium, thorium, cerium, lanthanum, or a mixture thereof.

Embodiment 7 is a process that includes the features of any one of embodiments 1-6, in which the combustion zone comprises a radiative section and a convective section and the carbon dioxide and one or more volatile organic compound by-products are fed to the convective section of the combustion zone.

Embodiment 8 is a process that includes the features of any one of embodiments 1-7, in which step (iii) comprises cooling the gaseous product mixture by contact with a heat exchanger or a solvent.

Embodiment 9 is a process that includes the features of any one of embodiments 1-8, in which step (iii) comprises contacting the gaseous product mixture with water in a counter-current absorber.

Embodiment 10 is a process that includes the features of any one of embodiments 1-9, in which about 50 to 100 weight percent of the one or more volatile organic compound by-products, based on the total weight of the volatile organic compounds by-products fed to the combustion zone, is converted to carbon dioxide in the combustion zone of the direct-fired furnace.

Embodiment 11 is a process that includes the features of any one of embodiments 1-10, in which the vaporized feed stream in step (i) comprises acetic acid and the superheated feed stream has a temperature of about 350 to about 600° C.; the catalyst of step (ii) comprises one or more metal oxides of titanium, zirconium, lanthanum, cerium, thorium, or mixtures thereof, and the gaseous product mixture comprises carbon dioxide, acetone, and one or more volatile organic compound by-products; the separation of step (iii) comprises contacting the gaseous product mixture with an absorption solvent to produce a crude liquid absorbent stream comprising a major portion of the acetone in the gaseous product mixture and a gaseous by-product stream comprising carbon dioxide, a minor portion of the acetone in the gaseous product mixture, and the one or more volatile organic compound by-products; and in which step (iv) comprises feeding a least a portion of the gaseous by-product stream to the combustion zone of the direct-fired furnace, wherein the combustion zone contains sufficient oxygen for complete combustion of the acetone and the one or more volatile organic compound by-products present in the gaseous by-product stream fed to the combustion zone.

Embodiment 12 is a process that includes the features of embodiment 11, in which vaporized feed stream further comprises about 70 to about 100 weight percent acetic acid and about 0 to about 30 weight percent water.

Embodiment 13 is a process that includes the features of any one of embodiments 11-12, in which the one or more volatile organic compound by-products comprise isobutylene, methane, hydrogen, or mixtures thereof.

Embodiment 14 is a process that includes the features of any one of embodiments 11-13, in which the combustion zone of the direct-fired furnace contains about 10 to about 40 mole percent excess oxygen over the amount required for complete combustion of the acetone and one or more volatile organic compound by-products present in the gaseous by-product stream fed to the combustion zone.

Embodiment 15 is a process that includes the features of any one of embodiments 11-14, in which the combustion zone comprises a radiative section and a convective section and the residence time of the one or more volatile organic compound by-products in the convective section of the combustion zone is about 0.02 to about 5 seconds.

Embodiment 16 is a process that includes the features of any one of embodiments 11-15, in which the catalyst further comprises about 0.05 to about 50 weight percent lithium, sodium, calcium, potassium, cesium, or mixtures thereof, based on the total weight of the catalyst, and has a surface area of about 10 to about 400 $m^2/g$ of catalyst.

Embodiment 17 is a process that includes the features of any one of embodiments 11-16, in which step (iii) comprises contacting the gaseous product mixture from step (ii) with water to produce a liquid absorbent stream comprising a major portion of acetone in the gaseous product mixture and a gaseous by-product stream comprising carbon dioxide, a minor portion of the acetone in the gaseous product mixture, and the one or more volatile organic compound by-products; and further comprises (v) distilling the liquid absorbent stream to produce a distillate comprising a refined acetone product and a distillation bottoms comprising water.

Embodiment 18 is a process that includes the features of embodiment 17, in which step (ii) is carried out in a single or multiple stage adiabatic fixed bed reactor having a temperature of about 300 to about 600° C. over the length of the reactor and an inlet pressure of about 0.7 to about 9 bars absolute.

Embodiment 19 is a process that includes the features of any one of embodiments 17-18, in which the catalyst comprises one or more metal oxides of titanium, zirconium, cerium, thorium, lanthanum, or mixtures thereof, and has a surface area of about 50 to about 200 $m^2/g$.

Embodiment 20 is a process that includes the features of any one of embodiments 17-19, in which the weight to weight ratio of gaseous product mixture contacted with water is about 0.5:1 to about 3:1 and the liquid absorbent stream comprises about 20 to about 65 weight percent acetone, based on the total weight of the liquid absorbent stream, about 35 to about 75 weight percent water, 0 to about 3 weight percent acetic acid, and about 0.1 to about 2 weight percent mesityl oxide, isophorone, mesitylene, or a mixture thereof.

Embodiment 21 is a process that includes the features of any one of embodiments 17-20, in which the refined acetone product comprises about 95 to about 100 weight percent acetone and about 0 to about 5 weight percent water, based on the total weight of the refined acetone product.

The invention is further illustrated by the following examples.

EXAMPLES

Example 1

Preparation of Acetone by Ketonization of Acetic Acid

Three GC methods were employed to analyze the ketonization process samples: GC method 1 used a DB-Wax (60 m×0.32 mm×1.0 um) capillary column and a thermal conductivity detector (TCD). Samples were diluted in an internal standard solution that was directly injected onto the GC column. This method provided weight percent of acetaldehyde, propionaldehyde, isobutyraldehyde, n-butyraldehyde, diethyl ether, acetone, water, isopropyl acetate, methyl ethyl ketone, isopropanol, isopropyl propionate, methyl propyl ketone, diethyl ketone, methyl isobutyl ketone, butyl acetate, mesityl oxide, dipropyl ketone, methyl amyl ketone, mesitylene, diacetone alcohol, and isophorone.

For the determination of weight percent organic acids, each sample was also analyzed by the following GC method 2 that used a DB-1 (60 m×0.32 mm×1.0 um) capillary column and a flame ionization detector (FID). The sample was first derivatized by reacting with BSTFA [N,O-bis(trimethylsilyl) trifluoroacetamide], which converted any organic acids present in the sample into their corresponding trimethylsilyl (TMS) esters. This method provided the weight percentage of acetic acid, propionic acid, isobutyric acid, butyric acid, and formic acid. This method was also used to determine the weight percentage of alcohols (as TMS-ethers) and ketones (ketones were not derivatized by contact with BSTFA and were analyzed without derivatization).

GC method 3 was used to measure ppm levels of impurities in the final distilled acetone samples. This method used multiple GC columns: DB-Waxtre (60 m×0.32 mm×1.0 um), DB-1 (60 m×0.32 mm×1.0 um), and DB-1301 (60 m×0.32 mm×1.0 um) with dual FID and a mass selective detector (GC/MS). Aldehydes, alcohols, esters, and ketones at ppm concentration levels were quantified by the dual column GC/FID method and other ppm-level impurities were identified and estimated by GC/MS.

A typical experimental ketonization procedure follows. Glacial acetic acid, comprising less than 0.5 weight percent of propionic acid, butyric acid, and other high boilers, was mixed with water to produce a wet acid feed stream comprising 90.2 wt % acetic acid and 9.8 weight percent water. A 316 SS tubular ketonization reactor, 1.5" ID×24" L, with thermocouples located every 2" in the reactor, was charged with 475.6 grams of a $TiO_2$ (anatase)/4% graphite (as binder) formed into 3/16" catalyst pellets. The depth of the catalyst bed was 12 inches. Quartz chips were loaded to a depth of 12 inches below and two inches above the catalyst bed. The reactor was wrapped with band insulation (about 1/8" thick), followed by electrical heat tape, and then covered in 6" of high temperature insulation. The reactor was connected via 1/2" 316 SS tubing to an electrically heated tubing section acting as a vaporizer, which was connected, in turn, to an vaporizer unit comprising a 316 SS 1½" ID×24" tube fitted with a 150-watt band heater, insulation, a dual-barrel syringe pump, and a level-controlled piston sludge pump.

During operation of the reactor, the feed acid was pumped continuously to the vaporizer at a rate of 11.7 g/min. The temperature of the vaporizer was approximately 135° C. throughout the run. The feed acid was sludged out of the vaporizer at a rate averaging 19.9 weight percent of the feed flow. The sludged acid was found to contain about 94.1 weight percent acetic acid. The vaporized wet acid stream, comprising about 89.1 weight percent acetic acid and about 10.9 weight percent water, was then heated in the superheat section to about 440° C. and passed to the ketonization reactor at flow rate of about 9.4 grams/minute. The ketonization reactor was operated in near-adiabatic mode (the heat tape added only sufficient heat to overcome non-reactive heat losses); the average temperature of the catalyst bed was about 420° C.

The reactor effluent was condensed at 17° C. and allowed to collect in an overflow tank. The off-gas from the tank was further contacted countercurrently with fresh water in an absorber. The absorber comprised an insulated, 8 ft×1", 316 SS tube filled with 1/8" 316 SS Penn State packing. The fresh water was fed at a rate of 10 ml/min to the top of the absorber. A portion of the underflow from the absorber was passed through a water-cooled tube-in tube exchanger (temperature of 17° C.) and circulated at a rate of 36 ml/min to the center section of the column. The off gas from the absorber was passed through a dry ice trap to condense additional water and acetone. The volume of the off gas from the dry ice trap was measured by a flow meter and analyzed by gas chromatography as described above. The remainder of the underflow stream, comprising acetone, water, and other heavy impurities, was combined with the overflow from the reactor condensation pot, and the dry ice trap liquids into a product tank. The contents of the product tank were weighed every 24 hours and analyzed by gas chromatography by the GC methods described above.

The ketonization reactor was operated continuously for 1128 hours, with a total feed to the vaporizer of 636 kilograms of acetic acid-water feed mixture. Conversion of acetic acid over the course of the run was 99.7%. A total of 875.7 kilograms of material was collected from the product tank over the course of the run and had the overall composition shown in Table 1. A total of 94,832 standard cubic liters of carbon dioxide off gas, with the composition shown in Table 2, was also generated during operation. The weight percentages in Tables 1 and 2 have not been normalized to give a total of 100 weight percent.

TABLE 1

| Condensed Reactor Effluent Composition | |
|---|---|
| Component | Weight % |
| Acetone | 32.76% |
| Acetic Acid | 0.22% |
| Water | 66.72% |
| Mesityl Oxide | 0.25% |
| Mesitylene | 0.0002% |
| Isophorone | 0.02% |
| Methyl ethyl Ketone | 0.0015% |
| Others | 0.044% |

TABLE 2

| Reactor Off-Gas Composition | |
|---|---|
| Component | Mole % |
| Hydrogen | 0.06% |
| Carbon dioxide | 98.53% |
| Methane | 0.10% |
| Acetone | 0.04% |
| isobutylene | 0.11% |

TABLE 2-continued

| Reactor Off-Gas Composition | |
|---|---|
| Component | Mole % |
| Water | 1.15% |
| MEK and other by-products | 0.01% |

Example 2

Combustion of VOC's

Kinetic expressions were found in the literature describing the rate of combustion of VOC's, such as MEK, methane, and isobutylene, as a function of temperature under typical furnace conditions with excess oxygen present. These expressions were used to determine the temperature and residence time needed to achieve a given conversion of the VOC's of interest. All reactions were assumed to be isothermal and follow first order kinetics, such that the extent of conversion can be calculated as follows:

$$X = e^{(kT)}$$

wherein X is the extent of reaction, k is the first order rate constant, with units of 1/time, and T is the reaction temperature, in units of temperature, such as degrees kelvin. The results are shown in Table 3 below.

TABLE 3

Temperature-Dependent Residence Time
Required for Given Conversion of VOC

| Temp, | | Residence Time required for given conversion, sec | | | |
|---|---|---|---|---|---|
| ° C. | % Conv | Methane | i-Butene | MEK | Acetone |
| 600 | 50% | 0.921 | 0.687 | 1.987 | 1.388 |
| 650 | 50% | 0.198 | 0.112 | 0.321 | 0.226 |
| 700 | 50% | 0.050 | 0.022 | 0.063 | 0.044 |
| 750 | 50% | 0.014 | 0.005 | 0.014 | 0.010 |
| 800 | 50% | 0.005 | 0.001 | 0.004 | 0.003 |
| 600 | 70% | 1.599 | 1.192 | 3.451 | 2.411 |
| 650 | 70% | 0.343 | 0.194 | 0.557 | 0.392 |
| 700 | 70% | 0.086 | 0.038 | 0.109 | 0.077 |
| 750 | 70% | 0.025 | 0.009 | 0.025 | 0.018 |
| 800 | 70% | 0.008 | 0.002 | 0.007 | 0.005 |
| 600 | 90% | 3.059 | 2.281 | 6.601 | 4.610 |
| 650 | 90% | 0.656 | 0.371 | 1.066 | 0.749 |
| 700 | 90% | 0.165 | 0.073 | 0.208 | 0.147 |
| 750 | 90% | 0.047 | 0.017 | 0.047 | 0.034 |
| 800 | 90% | 0.015 | 0.004 | 0.012 | 0.009 |
| 600 | 95% | 3.980 | 2.967 | 8.588 | 5.998 |
| 650 | 95% | 0.854 | 0.482 | 1.387 | 0.975 |
| 700 | 95% | 0.215 | 0.094 | 0.270 | 0.191 |
| 750 | 95% | 0.062 | 0.022 | 0.062 | 0.044 |
| 800 | 95% | 0.020 | 0.006 | 0.016 | 0.012 |

Example 3

Material Balance Around Direct-Fired Furnace

A computer process simulation was developed in ASPEN to model the direct-fired furnace/superheater. A feed comprising 557.7 kmol/hr of wet acid from the vaporizer, temperature of 145° C., of composition similar to the experimental feed described in Example 1 above, was fed through the superheater to produce a superheated acid stream at 425° C. The superheater was designed to supply 0.8 million J/kg of acid fed. Natural gas and containing a 33% molar excess of air required for complete combustion, were combusted in the furnace, and mixed in the post combustion zone of the furnace with a by-product carbon dioxide stream having a composition similar to that described in Table 2 and a volume commensurate with the expected conversion and selectivity of the given acid feed rate. The residence time in the post combustion zone was 0.1 second at a temperature of 700° C. A material balance around the superheater is shown in Table 4. Stream numbers are in reference to FIG. 2. Conversions of VOC's are given in Table 5.

TABLE 4

Superheater Material Balance, Kmoles/hr

| | Stream Number | | | | | |
|---|---|---|---|---|---|---|
| | 19 | 14 | 13 | 12 | 11 | 15 |
| Temperature (° C.) | 27.32 | 312 | 30 | 30 | 145.1 | 425 |
| Pressure (bara) | 15.82 | 15.49 | 14.57 | 14.57 | 16.96 | 16.79 |
| $CO_2$ | 200.773 | 234.408 | 0.000 | 0.000 | 0.000 | 0.000 |
| i-Butene | 0.224 | 0.009 | 0.000 | 0.000 | 0.000 | 0.000 |
| Acetone | 0.082 | 0.017 | 0.000 | 0.000 | 0.000 | 0.000 |
| Water | 2.343 | 67.401 | 0.000 | 0.000 | 150.943 | 150.943 |
| Acetic Acid | 0.000 | 0.000 | 0.000 | 0.000 | 405.695 | 405.695 |
| $O_2$ | 0.000 | 22.125 | 88.000 | 0.000 | 0.000 | 0.000 |
| $N_2$ | 0.000 | 378.258 | 378.151 | 0.000 | 0.000 | 0.000 |
| Propionic acid | 0.000 | 0.000 | 0.000 | 0.000 | 0.083 | 0.083 |
| n-Butyric Acid | 0.000 | 0.000 | 0.000 | 0.000 | 0.181 | 0.181 |
| MEK | 0.020 | 0.007 | 0.000 | 0.000 | 0.034 | 0.034 |
| Other High Boilers | 0.000 | 0.000 | 0.000 | 0.000 | 0.777 | 0.777 |
| $H_2$ | 0.122 | 0.000 | 0.000 | 0.000 | 0.000 | 0.000 |
| Methane | 0.204 | 0.050 | 0.000 | 32.375 | 0.000 | 0.000 |
| $NO_2$ | 0.000 | 0.017 | 0.000 | 0.000 | 0.000 | 0.000 |
| $H_2S$ | 0.000 | 0.000 | 0.000 | 0.001 | 0.000 | 0.000 |
| $SO_2$ | 0.000 | 0.001 | 0.000 | 0.000 | 0.000 | 0.000 |
| Total Kmoles/hr | 203.768 | 702.293 | 466.151 | 32.376 | 557.714 | 557.714 |

TABLE 5

Calculated VOC Conversions at 0.1
second Residence Time and 700° C.

| Compound | % Combustion |
|---|---|
| i-Butene | 96% |
| Acetone | 79% |
| MEK | 67% |
| H2 | 100% |
| Methane | 75% |

We claim:

1. A process for reducing the emission of volatile organic compounds from a ketonization process, comprising
   (i). heating a vaporized feed stream comprising one or more carboxylic acids in a direct-fired furnace comprising a combustion zone to produce a superheated feed stream;
   (ii). contacting the superheated feed stream with a metal oxide catalyst to form a gaseous product mixture comprising one or more ketones, carbon dioxide, and one or more volatile organic compound by-products;
   (iii). separating the one or more ketones from the carbon dioxide and one or more volatile organic compound by-products; and
   (iv). feeding at least a portion of the carbon dioxide and the one or more volatile organic compound by-products to the combustion zone of the direct-fired furnace.

2. The process according to claim 1, wherein the one or more carboxylic acids comprise a carboxylic acid having 2 to 20 carbon atoms.

3. The process according to claim 1, wherein the one or more carboxylic acids comprise acetic acid, propionic acid, butyric acid, isobutyric acid, valeric acid, hexanoic acid, heptanoic acid, octanoic acid, 2-ethyl hexanoic acid, nonanoic acid, or a mixture thereof.

4. The process according to claim 1, wherein the one or more carboxylic acids comprise acetic acid, the one or more ketones comprise acetone, and the one or more volatile organic compound by-products comprise isobutylene, methane, hydrogen, or mixtures thereof.

5. The process according to claim 1, wherein step (ii) is carried out in fixed bed, adiabatic reactor.

6. The process according to claim 1, wherein the superheated feed stream has a temperature of about 350 to about 650° C. and the metal oxide catalyst comprises an oxide of titanium, zirconium, thorium, cerium, lanthanum, or a mixture thereof.

7. The process according to claim 1, wherein the combustion zone comprises a radiative section and a convective section and the carbon dioxide and one or more volatile organic compound by-products are fed to the convective section of the combustion zone.

8. The process according to claim 1, wherein step (iii) comprises cooling the gaseous product mixture by contact with a heat exchanger or a solvent.

9. The process according to claim 8, wherein step (iii) comprises contacting the gaseous product mixture with water in a countercurrent absorber.

10. The process according to claim 1, wherein about 50 to 100 weight percent of the one or more volatile organic compound by-products, based on the total weight of the volatile organic compounds by-products fed to the combustion zone, is converted to carbon dioxide in the combustion zone of the direct-fired furnace.

11. A process for reducing the emission of volatile organic compounds from the production of acetone, comprising
   (i). heating a vaporized feed stream comprising acetic acid in a direct-fired furnace comprising a combustion zone to produce a superheated feed stream having a temperature of about 350 to about 550° C.;
   (ii). contacting the superheated feed stream with a catalyst comprising one or more metal oxides of titanium, zirconium, lanthanum, cerium, thorium, or mixtures thereof to produce a gaseous product mixture comprising carbon dioxide, acetone, and one or more volatile organic compound by-products;
   (iii). contacting the gaseous product mixture with an absorption solvent to produce a crude liquid absorbent stream comprising a major portion of the acetone in the gaseous product mixture and a gaseous by-product stream comprising carbon dioxide, a minor portion of the acetone in the gaseous product mixture, and the one or more volatile organic compound by-products; and
   (iv). feeding a least a portion of the gaseous by-product stream to the combustion zone of the direct-fired furnace, wherein the combustion zone contains sufficient oxygen for complete combustion of the acetone and the one or more volatile organic compound by-products present in the gaseous by-product stream fed to the combustion zone.

12. The process according to claim 11, wherein the vaporized feed stream further comprises about 70 to about 100 weight percent acetic acid and about 0 to about 30 weight percent water.

13. The process according to claim 11, wherein the one or more volatile organic compound by-products comprise isobutylene, methane, hydrogen, or mixtures thereof.

14. The process according to claim 11, wherein the combustion zone of the direct-fired furnace contains about 10 to about 40 mole percent excess oxygen over the amount required for complete combustion of the acetone and one or more volatile organic compound by-products present in the gaseous by-product stream fed to the combustion zone.

15. The process according to claim 11, wherein the combustion zone comprises a radiative section and a convective section and the residence time of the one or more volatile organic compound by-products in the convective section of the combustion zone is about 0.02 to about 5 seconds.

16. The process according to claim 11, wherein the catalyst further comprises about 0.05 to about 50 weight percent lithium, sodium, calcium, potassium, cesium, or mixtures thereof, based on the total weight of the catalyst, and has a surface area of about 10 to about 400 $m^2/g$ of catalyst.

17. A process for the preparation of acetone, comprising
   (i). heating a vaporized feed stream comprising acetic acid in a direct-fired furnace comprising a combustion zone to produce a superheated feed stream having a temperature of about 350 to about 650° C.;
   (ii). contacting the superheated feed stream with a catalyst comprising one or more metal oxides to produce a gaseous product mixture comprising carbon dioxide, acetone, and one or more volatile organic compound by-products;
   (iii). contacting the gaseous product mixture with water to produce a liquid absorbent stream comprising a major portion of the acetone in the gaseous product mixture and a gaseous by-product stream comprising carbon dioxide, a minor portion of the acetone in the gaseous product mixture, and the one or more volatile organic compound by-products;
   (iv). feeding a least a portion of the gaseous by-product stream to the combustion zone of step (i); and
   (v). distilling the liquid absorbent stream to produce a distillate comprising a refined acetone product and a distillation bottoms comprising water.

18. The process according to claim 17, wherein step (ii) is carried out in a single or multiple stage adiabatic fixed bed reactor having a temperature of about 300 to about 600° C. over the length of the reactor and an inlet pressure of about 0.7 to about 9 bars absolute.

19. The process according to claim 17, wherein the catalyst comprises one or more metal oxides of titanium, zirconium, cerium, thorium, lanthanum, or mixtures thereof, and has a surface area of about 50 to about 200 $m^2/g$.

20. The process according to claim 17, wherein the weight to weight ratio of gaseous product mixture contacted with water is about 0.5:1 to about 3:1 and the liquid absorbent stream comprises about 20 to about 65 weight percent acetone, based on the total weight of the liquid absorbent stream, about 35 to about 75 weight percent water, 0 to about 3 weight percent acetic acid, and about 0.1 to about 2 weight percent mesityl oxide, isophorone, mesitylene, or a mixture thereof.

21. The process according to claim 17, wherein the refined acetone product comprises about 95 to about 100 weight percent acetone and about 0 to about 5 weight percent water based on the total weight of the refined acetone product.

* * * * *